United States Patent [19]

Johnson et al.

[11] Patent Number: 4,593,146
[45] Date of Patent: Jun. 3, 1986

[54] ISOMERIZATION PROCESS AND CATALYST THEREFOR

[75] Inventors: Marvin M. Johnson; Gerhard P. Nowack; Max P. McDaniel, all of Bartlesville, Okla.

[73] Assignee: Phillips Petroleum Company, Bartlesville, Okla.

[21] Appl. No.: 718,241

[22] Filed: Mar. 29, 1985

[51] Int. Cl.$^4$ .............................................. C07C 5/25
[52] U.S. Cl. .................................. 585/667; 585/664; 585/670; 585/671
[58] Field of Search ................ 585/667, 664, 670, 671

[56] References Cited

U.S. PATENT DOCUMENTS

| | | | |
|---|---|---|---|
| 3,310,598 | 3/1967 | Noddings et al. | 585/667 |
| 3,879,310 | 4/1975 | Rigge et al. | 585/667 |
| 3,904,550 | 9/1975 | Pine | 585/667 |
| 4,364,839 | 12/1982 | McDaniel et al. | 585/510 |
| 4,409,418 | 10/1983 | Johnson et al. | 585/667 |
| 4,527,001 | 7/1985 | Kaiser | 585/671 |

Primary Examiner—John Doll
Assistant Examiner—A. Pal
Attorney, Agent, or Firm—Stephen E. Reiter

[57] ABSTRACT

Aliphatic olefinic hydrocarbons are isomerized in the presence of a catalyst consisting essentially of elemental chromium or a chromium compound and an aluminum phosphate support wherein the phosphorus/aluminum atomic ratio of the support is less than 1.

7 Claims, No Drawings

ISOMERIZATION PROCESS AND CATALYST THEREFOR

This invention relates to the isomerization of olefinic compounds. In one aspect, the invention relates to processes for the double bond isomerization of mono-olefins. In another aspect, the invention relates to catalysts for the double bond isomerization of mono-olefins.

BACKGROUND

Double bond isomerization, i.e., the shifting of the position of a double bond in an olefinic compound, is a well known phenomenon. Such an operation is frequently valuable in the conversion of one olefinic compound to one or more isomers thereof which may be less plentiful and more valuable. Olefinic compounds as a class are useful in themselves, such as for use as monomers to produce a wide variety of polymeric compositions, or for use as building blocks to prepare other still more valuable compounds.

A number of catalysts are known in the art to be active in double bond isomerization. However, such double bond isomerization is frequently accompanied by undesirable side reactions such as cracking, dehydrogenation, polymerization, and the like.

OBJECTS OF THE INVENTION

An object of the invention, therefore, is a process for the double bond isomerization of olefins which causes minimum by-product formation so that high selectivity for double bond isomerized product is obtained.

It is another object of the invention to provide catalysts useful for double bond isomerization reactions.

These and other objects of the invention will become apparent from the disclosure and claims provided herein.

STATEMENT OF THE INVENTION

In accordance with the present invention, we have discovered that a catalyst consisting essentially of elemental chromium or a chromium compound and a phosphorus deficient aluminum phosphate support, i.e., support having a phosphorus/aluminum atomic ratio of less than 1, is an active and selective double bond isomerization catalyst.

DETAILED DESCRIPTION OF THE INVENTION

In accordance with one embodiment of the present invention, solid isomerization catalyst is provided consisting essentially of 0.1-10 weight percent of a supported chromium compound, calculated as chromium metal and based on the total weight of chromium and support, and aluminum phosphate support; wherein the phosphorus/aluminum atomic ratio of the support is less than 1, i.e., the aluminum phosphate support is phosphorus deficient.

In accordance with another embodiment of the present invention, a process for the double bond isomerization of aliphatic olefinic hydrocarbon feeds is provided which comprises contacting the feed under isomerization conditions with a chromium-aluminum phosphate catalyst as described hereinabove.

Any suitable method can be used to prepare the phosphorus deficient aluminum phosphate supports employed in the practice of the present invention.

Three suitable methods are set out hereinafter. First, an aluminum salt can be combined with a source of phosphate ions in an aqueous medium and neutralized with a neutralizing agent to give a hydrogel. Alternatively, a polar organic solvent can be used.

The aluminum salt employed is not critical, provided only that it does not contain an anion which will form a precipitate in the subsequent precipitation step. Aluminum nitrate and aluminum halides, particularly aluminum chloride, are the aluminum salts of choice for use in the invention. While certain phosphate salts such as triammonium ortho-phosphate can be used as the source of the $PO_4^{3-}$ ions, ortho-phosphoric acid is the source of choice for providing the $PO_4^{3-}$ ions.

The amorphous aluminum phosphate precipitate is prepared by neutralizing the acidic medium containing aluminum cations and phosphate anions. When the pH is increased to 2 or higher, the aluminum phosphorus moieties precipitate from the aqueous medium. While in theory the neutralization can be carried out by mixing the acidic solution with an appropriate alkali in any manner, it is preferred to simultaneously add the acidic medium and the neutralizing alkali to a stirred aqueous medium. The two solutions should be added at controlled rates so that the pH is continuously maintained at a preselected pH in the range of about 4.0–11.0 and preferably about 6.0–10.0. While a wide variety of bases can be used to neutralize the acidic medium, it is preferred to use ammonium hydroxide or an ammonium salt such as ammonium carbonate so that the aluminum phosphorous precipitate will be free of metallic ions that might be incorporated into the precipitate, if inorganic bases such as sodium carbonate or sodium hydroxide were used in the process. While the precipitation reaction can be carried out over a wide range of temperatures, ambient temperature usually is employed, as no significant advantages are obtained by heating or cooling.

After the precipitation is completed, the precipitate is filtered, washed one or more times to free the precipitate of occluded ions, and dried. After drying, the precipitate is optionally calcined in a conventional manner at a suitable temperature, typically in a range of about 125°–500° C.

The calcined aluminum phosphate product is amorphous, and usually has a bulk density in the range of about 0.23 to 0.5 grams/cm³, and has the appearance of a compacted mass of spherical granules having a diameter in the 1–5 micron range.

As certain aluminum salts, ortho-phosphoric acid and ammonium hydroxide are soluble in certain polar solvents such as methanol, it is possible to prepare the previously described inorganic carriers by carrying out the indicated synthesis steps in such polar solvents or in mixtures of water and such polar solvents.

The second method for forming the base of the catalyst system of this invention is to combine an aluminum alkoxide with an aqueous solution containing phosphate ions.

The aluminum alkoxides used herein may include any alkoxide which contains from 1 to 20, preferably 2 to 4 carbon atoms in the alkoxide group and which is soluble in the liquid reaction medium. Specific examples of suitable aluminum alkoxides include, among others, aluminum sec-butoxide, aluminum ethoxide, aluminum isopropoxide, aluminum propoxide, aluminum n-butoxide and aluminum iso-butoxide. Mixed aluminum alkoxides such as those produced by oxidizing the growth product from the reaction of aluminum triethyl and ethylene are also suitable.

The phosphate ions which are reacted with the aluminum alkoxide may be derived from a phosphorus-containing acid such as the phosphoric, phosphorus and phosphonic acids. These acids may be characterized as having the formula:

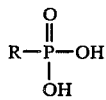

wherein R represents a hydroxyl group, hydrogen or an organic radical such as hydrocarbon radicals including alkyl, cycloalkyl, aryl, aralkyl or alkaryl and the like, containing from 1 to 12 carbon atoms. Suitable phosphorus-containing acids can include phosphoric and/or phosphorus (including hypo, meta and pyro forms thereof) acid, methylphosphonic acid, ethylphosphonic acid, hexylphosphonic acid, phenylphosphonic acid, alkylsubstituted-phenylphosphonic acid, cyclohexylphosphonic acid, alkylsubstituted-cyclohexylphosphonic acid, and the like. The halogen substituted forms of the aforementioned acids may also be used such as, for example, monofluorophosphoric acid ($H_2PO_3F$). The preferred acids are phosphoric and phosphorous acids. Soluble salts of these acids such as the ammonium, alkyl ammonium, sodium and potassium salts thereof may also be used.

The aluminum alkoxide and phosphorus-containing acid are reacted in the presence of a suitable solvent and water at a temperature ranging from ambient to the boiling point of the reaction mixture, usually in the range of 20° to 100° C., for a sufficient period of time to complete the desired reaction, usually for a period of 1 to 4 hours. The molar ratio of phosphate ions to aluminum alkoxide charged to the reaction mixture will be in the broad range of 0.2:1 to 1:1. Preferably, the relative amounts of reactants will be adjusted to give a molar ratio of about 0.6:1 to 0.9:1. The amount of water utilized in the reaction is that calculated to hydrolyze the aluminum alkoxide that is not consumed by the source of phosphate ions in the reaction mixture. Usually a 10 percent molar excess of water is added to ensure complete reaction.

The reaction is preferably conducted in the presence of an organic liquid which is insert to the reactants and acts as a solvent for the system. Suitable solvents include, among others, the $C_1$-$C_4$ alcohols such as methanol, ethanol, i-propanol, n-propanol, n-butanol, isobutanol, sec-butanol, and t-butanol. The amount of solvent used may range from 0 to 200, preferably 50 to 100 volume parts per volume part of alkoxide.

After the reaction is complete, the precipitate which has formed can be filtered or dried by other techniques known by those of skill in the art. The phosphorus deficient aluminum phosphate can then be combined with a catalytic amount of a suitable chromium compound, as described more fully below. Calcination of the aluminum phosphate product is conveniently effected by heating at 800° to 1,200° F. for a period of 1 to 4 hours.

For the third method of forming the base of the catalyst system of the invention, an aluminum salt which will melt can be used, with the source of phosphate ions combined with the melt and then neutralized to give the hydrogel. Generally those aluminum salts with a sufficiently low melting point are hydrated. Orthophosphoric acid, orthophosphates such as monoammonium phosphate and diammonium hydrogen phosphate or mixtures of monoammonium and diammonium phosphate are preferred sources of phosphate ions. The scope of the phosphate ions source can be the same as in the first method. In a variation of this third method, a concentrated syrup of an aluminum salt is used. Thus, the third method can be broadly viewed as employing a concentrated mass of the acid phase (source of aluminum and source of orthophosphate ions). Alternatively, in method three and possibly method one, the aluminum-phosphate composition can be only partially neutralized and allowed to sit as a strongly acid composition until gellation occurs spontaneously.

In the preparations involving an aqueous medium, it is preferred to remove water by azeotropic distillation or by washing it with a volatile, water miscible, low surface tension organic liquid. In the techniques not employing water or a solvent, any small amount of water carried over from water of hydration or from the base used in the neutralization can be removed by conventional spray drying, tray drying or oven drying, thus avoiding the necessity for azeotropic distillation. However, even in these situations, if it is desired to water wash the hydrogel, then azeotropic distillation or washing with a volatile oxygen containing water miscible solvent is desirable. After drying of water in this manner, the gel is preferably dried of solvent under mild conditions, for instance, by heating at a temperature of 25° to 110° C., most preferably under vacuum.

It may be desirable in some instances to coprecipitate other materials with the phosphate or have other materials present during the gellation. For instance, the chromium compound such as chromium nitrate can be introduced with the reactants. Additional suitable chromium compounds include chromium nitrate, chromium sulfate, chromium acetate, chromium oxide, chromium hydroxide, chromium oxalate, and the like as well as mixtures of any two or more thereof.

The neutralization in the first and third methods can be carried out either by adding the acid phase to the base phase or vice versa (or by adding both to a third vessel). One suitable practice is to drip the acid phase into the base phase. This results in the production of smaller spheres or balls of the orthophosphate, particularly with the third method where the melt of aluminum salt and source of phosphate ions is dripped or sprayed or otherwise slowly added to a large excess of ammonium hydroxide. The spheres are subsequently collected, washed, dried and calcined.

Gellation occurs spontaneously at a pH of about 4, which is achieved by combining about 72 percent of the neutralizing agent, and it has been found, particularly in technique three, that this is undesirable. Therefore, neutralization is preferably achieved by either: (1) combining slowly with stirring about 72 percent of the amount of neutralizing agent needed for complete neutralization and aging until gellation occurs which will generally be 1 minute to 48 hours, more generally 5 minutes to 10 hours, more generally 10 minutes to 3 hours; thus gellation occurs at a pH below 4, generally about 2. While any base can be used, concentrated ammonium hydroxide, ammonia gas, or ammonia dissolved in an alcohol or other non-aqueous solvent are preferred. Other suitable neutralizing agents include ammonium carbonate used alone or in combination, ethylene oxide and propylene oxide. Alternatively, in techniques one and three, particularly one, the phosphate can be in the neutralizing agent.

The chromium can be coprecipitated as noted hereinabove or can be added to the hydrogel. For example, a water soluble chromium compound, such as chromium nitrate, chromium acetate, or $CrO_3$ can be added to the hydrogel. Alternatively, a chromium compound soluble in an anhydrous solvent such as hydrocarbon can be used to impregnate the xerogel prior to activation. Suitable chromium compounds for such anhydrous impregnation include tertiary-butyl chromate. The chromium compounds are used in amounts sufficient to give 0.001 to 10, preferably 0.1 to 5, more preferably about 1 weight percent chromium based on the weight of the xerogel base. The term xerogel as used herein refers to the predominantly amorphous gel resulting from the removal of free water from the hydrogel.

The activation of the thus-formed xerogel can be carried out at temperatures in the range of 150°–800° C. The activating ambient can be any oxidizing ambient but for convenience and economy, an oxygen-containing ambient such as air is preferred. Times of 5 minutes to 24 hours, preferably 0.5 to 10 hours, are suitable for the activation or calcining step.

The aluminum and phosphorus components are selected so as to give an atom ratio of phosphorus to aluminum within the range of 0.2:1 to 1:1, preferably 0.6:1 to 0.9:1.

Aliphatic mono-olefins and poly-olefins having more than three carbon atoms are amenable to treatment by the catalyst of this invention, including branched chain as well as normal chain compounds. In general, olefins suitable for treatment in accordance with the present invention are aliphatic olefinic hydrocarbons having from 4 to about 20 carbon atoms, inclusive. Preferably, the practice of the present invention is carried out with a feed comprising mono-olefinic hydrocarbons.

Representative examples of mono-olefins useful in the practice of the present invention include butenes, pentenes, hexenes, octenes, decenes, and the like as well as mixtures of any two or more thereof.

In carrying out isomerization reactions with the catalyst of the invention, suitable reaction conditions or isomerization conditions can be used which effectively cause double bond isomerization of the olefins present in the feed. In general, the temperature at which isomerization is affected with this catalyst is about 300°–1100° F. Preferably the temperature will be in the range of about 500°–900° F. Reaction pressure can vary appreciably and can be subatmospheric. Preferably reaction pressure will not exceed about 500 psig in order to avoid condensation reactions that ultimately lead to excessive coke formation on the catalyst.

The isomerization reaction of the present invention can be carried out in both the liquid and gaseous phase. When reaction is carried out in the gas phase, contact time of reactants on the catalyst can be expressed as gas hourly space velocity (GHSV) and can range between about 100 to 1000. Preferably, GHSV will range between about 200 and 750. When the isomerization reaction of the present invention is carried out in the liquid phase, contact time of reactants on the catalyst can be expressed as liquid hourly space velocity (LHSV) and can range between about 0.1 and 10. Preferably LHSV will range between about 0.5 and 2.

A further understanding of the present invention and its advantages will be provided by reference to the following non limiting examples.

EXAMPLE I

Catalyst Preparation

The catalysts were prepared in three general methods and variations thereof.

In method A (the first method broadly described hereinabove), about 0.5 mole of $Al(NO_3)_3.9H_2O$ was dissolved in about 500 mL of deionized water and to it was added sufficient 85% $H_3PO_4$ to give the desired atomic ratio of P:Al. The resulting solution was neutralized by adding sufficient concentrated ammonium hydroxide to reach a pH of about 6–7. The white hydrogel precipitate was filtered off and washed with about 3 L of deionized water. The filter cake was dried in procedure (1) by simply placing it in a vacuum over at about 80° C. for a few hours. In a preferred procedure (2) the filter cake was dried of water by employing azeotropic distillation or washing with isoamyl alcohol to remove the water. Each product after removal of water was impregnated with a solution of chromium (III) acetate dissolved in an alcohol, such as methyl alcohol, sufficient to provide about 1 weight percent chromium based on the dry finished catalyst. Afterward the filter cake was dried of alcohol by heating at 60° C. in a vacuum over to remove the alcohol. Each catalyst was activated for isomerization by calcining in a fluidized bed with dry air for about 5 hours or more at the specified temperature.

Also, in place of or in admixture with the $H_3PO_4$, ammonium phosphates such as $NH_4H_2PO_4$ and $(NH_4)_2HPO_4$ can be used alone or mixtures thereof to furnish the desired amount of phosphate ions required to make the metal phosphate gels.

Another soluble aluminum salt such as aluminum acetate or sulfate can be substituted for the nitrate, if desired. Less preferable soluble aluminum salts such as the chloride can also be employed but the gels may require more thorough washing to remove most of the chloride anions.

Method B (the second method broadly described hereinabove) is a substantially anhydrous method. To a solution containing about ½ mole of aluminum triisopropoxide (or related alkoxide) dissolved in about 400 mL of dry isopropyl alcohol, for example, was added a solution containing about 200 mL of dry isopropyl alcohol, a little deionized water, e.g. 0.2 mole, and sufficient 85% $H_3PO_4$ to give the desired atomic ratio of P:Al. For example, with about 6.5 mL of 85% $H_3PO_4$ (0.095 mole), the P:Al atomic ratio is about 0.761:1. The resulting precipitate was isolated by filtering, and the filter cake was dried in a vacuum oven at about 80° C. The dry product was then impregnated anhydrously by contact with a methanol solution of chromium (III) acetate sufficient to provide about 1 weight percent chromium based on the dry, finished catalyst. The catalyst was activated by heating for the desired length of time, e.g. five hours, at the specified temperature in a fluidized bed in dry air. Method B is different in principle from methods A and C in that the gel forms on addition of the phosphoric acid.

Method C (the third method broadly described hereinabove) is presently preferred. It was generally carried out by heating the desired quantity of an aluminum salt such as $Al(NO_3)_3.9H_2O$, e.g., about 1 lb (454 g), to about 80° C. to form a melt. The desired quantity of an ammonium phosphate, e.g., NH$_4$H$_2$PO$_4$, was dissolved in the melt to provide the atomic ratio of P/Al needed, and finally the desired amount of chromium (III) acetate or chromium (III) nitrate was added to the melt mixture to provide about 1 weight percent chromium based on the weight of the dry, finished catalyst. Sufficient concentrated NH$_4$OH, e.g. 30 weight percent NH$_3$, was mixed with the melt mixture to neutralize it giving a pH of about 6–7. The resulting mixture was washed with sufficient deionized water to remove substantially all of the ammonium nitrate by-product and the washed product in turn was washed with isopropyl alcohol or other volatile water-miscible organic liquid to displace the water, or the washed product was azeotropically dried. The resulting product can be further dried in a vacuum oven, if desired, and activated as before in a fluidized bed in dry air for about 5 hours at the specified temperature.

In the catalyst preparation of Method C, the melt containing the Al(NO$_3$)$_3$.9H$_2$O, the NH$_4$H$_2$PO$_4$ and the Cr(NO$_3$)$_3$.9H$_2$O can be treated with NH$_4$OH to obtain a pH of about 6–7 to form the gel and the gel dried in the presence of the by-product NH$_4$NO$_3$. While this is essentially a nonaqueous system, there is a small amount of water present such that a sheet of pH indicator paper can be pressed into the gel and a pH reading obtained. The dry product can then be cautiously calcined to obtain the final catalyst. This procedure must be done carefully to avoid potential explosions or other undesired reactions.

Method C is fundamentally different from Methods A and B in that no added solvent is used, and the chromium is co-precipitated with the aluminum phosphate.

EXAMPLE II

Olefin Isomerization

Runs were made with several different catalysts to isomerize Phillips Pure Grade butene-1. Catalyst (−20+40 mesh) was placed in a ½" i.d. stainless steel reactor and the feed passed downflow at about 500–650 GHSV and atmospheric pressure. Reaction temperature, actual feed flow rate (as GHSV), weight of a 20 mL portion of catalyst used to charge the reactor and product analyses are presented in the Table. Products were analyzed by gas liquid chromatography (GLC).

TABLE

| Run # | Catalyst, g | Reaction Parameters | | Product Analysis, wt. %* | | |
|---|---|---|---|---|---|---|
| | | Temp., °F. | GHSV | 1-C$_4$ | t-2-C$_4$ | c-2-C$_4$ |
| 1 | MgO, 13.1 | 600 | 510 | 98.6 | 0.6 | 0.8 |
| | | 700 | 510 | 94.4 | 2.1 | 3.5 |
| 2 | 1% Cr/AlPO$_4$, 9.1 (P/Al = 0.8) | 600 | 650 | 17.9 | 47.1 | 35.0 |
| | | 700 | 650 | 18.0 | 46.3 | 35.7 |

TABLE-continued

| Run # | Catalyst, g | Reaction Parameters | | Product Analysis, wt. %* | | |
|---|---|---|---|---|---|---|
| | | Temp., °F. | GHSV | 1-C$_4$ | t-2-C$_4$ | c-2-C$_4$ |
| 3 | 1% Cr/AlPO$_4$, 7.5 (P/Al = 0.4) | 600 | 510 | 21 | 44 | 34 |

*1-C$_4$ is 1-butene
t-2-C$_4$ is trans-2-butene
c-2-C$_4$ is cis-2-butene

The results presented in the Table demonstrate that a chromium on phosphorus-deficient aluminum phosphate catalyst is very active for olefin isomerization. Thus, while control run 1, employing a known double bond isomerization catalyst, MgO, gave only about 1–5% feed conversion, invention runs 2 and 3 gave up to 80% conversion and higher on only one pass over the catalyst bed. In addition to the high double bond isomerization activity, the results indicate that little, if any, skeletal isomerization (to produce isobutylene) or carbon-carbon bond cleavage (to produce propylene) occurs during the invention isomerization process.

The examples have been provided merely to illustrate the practice of our invention and should not be read so as to limit the scope of our invention or the appended claims in any way. Reasonable variations and modifications, not departing from the essence and spirit of our invention, are contemplated to be within the scope of patent protection desired and sought.

We claim:
1. A process for the double bond isomerization of an aliphatic olefinic hydrocarbon feed which comprises contacting said feed under isomerization conditions with a catalyst consisting essentially of:
   (a) 0.1–10 wt.% of elemental chromium or a chromium compound, calculated as chromium metal and based on the total weight of chromium and support, and
   (b) an aluminum phosphate support wherein the phosphorus/aluminum atomic ratio of said support is less than one.
2. A process in accordance with claim 1 wherein said feed is an aliphatic mono-olefin hydrocarbon having 4–20 carbon atoms, inclusive.
3. A process in accordance with claim 2 wherein said aliphatic mono-olefin hydrocarbon is 1-butene.
4. A process in accordance with claim 1 wherein said isomerization conditions comprise a temperature in the range of about 300°–1100° F.
5. A process in accordance with claim 4 wherein said double bond isomerization is carried out in the gas phase at a gas hourly space velocity in the range of about 100–1000.
6. A process in accordance with claim 4 wherein said double bond isomerization is carried out in the liquid phase with a liquid hourly space velocity in the range of about 0.1–10.
7. A process in accordance with claim 1 wherein the phosphorus/aluminum atomic ratio of said aluminum phosphate support is in the range of 0.2–0.9:1.

* * * * *